United States Patent
Watanabe et al.

(10) Patent No.: US 8,598,029 B2
(45) Date of Patent: Dec. 3, 2013

(54) METHOD FOR FABRICATING FLIP-ATTACHED AND UNDERFILLED SEMICONDUCTOR DEVICES

(75) Inventors: Masako Watanabe, Oita (JP); Masazumi Amagai, Tsukuba (JP)

(73) Assignee: Texas Instruments Incorporated, Dallas, TX (US)

( * ) Notice: Subject to any disclaimer, the term of this patent is extended or adjusted under 35 U.S.C. 154(b) by 0 days.

(21) Appl. No.: 13/466,449

(22) Filed: May 8, 2012

(65) Prior Publication Data
US 2012/0220080 A1    Aug. 30, 2012

Related U.S. Application Data

(60) Continuation of application No. 12/703,267, filed on Feb. 10, 2010, now Pat. No. 8,193,085, which is a division of application No. 11/090,104, filed on Mar. 24, 2005, now Pat. No. 7,701,071.

(51) Int. Cl.
  *H01L 21/44*    (2006.01)
(52) U.S. Cl.
  USPC .......................... 438/612; 438/613; 257/782
(58) Field of Classification Search
  CPC ...... B23K 31/02; H01L 21/563; H01L 23/48; H01L 24/10; H01L 24/11; H01L 24/13; H01L 24/14; H01L 24/15; H01L 24/16; H01L 24/17

USPC ......... 438/108, 612, 613, 113, 455, 458, 460; 257/783, 778, 779, 780, E23.055, 782, 257/E23.021, E23.023
  See application file for complete search history.

(56) References Cited

U.S. PATENT DOCUMENTS

| 6,541,872 B1 * | 4/2003 | Schrock et al. ............... 257/783 |
| 2003/0199121 A1 * | 10/2003 | Caletka et al. ............... 438/113 |

* cited by examiner

*Primary Examiner* — Khiem D Nguyen
(74) *Attorney, Agent, or Firm* — Steven A. Shaw; W. James Brady; Frederick J. Telecky, Jr.

(57) ABSTRACT

A semiconductor device, which comprises a workpiece with an outline and a plurality of contact pads and further an external part with a plurality of terminal pads. This part is spaced from the workpiece and the terminal pads are aligned with the workpiece contact pads, respectively. A reflow element interconnects each of the contact pads with its respective terminal pad. Thermoplastic material fills the space between the workpiece and the part; this material adheres to the workpiece, the part and the reflow elements. Further, the material has an outline substantially in line with the outline of the workpiece, and fills the space substantially without voids. Due to the thermoplastic character of the filling material, the finished device can be reworked, when the temperature range for reflowing the reflow elements is reached.

7 Claims, 7 Drawing Sheets

METHOD FOR FABRICATING FLIP-ATTACHED AND UNDERFILLED SEMICONDUCTOR DEVICES

CROSS-REFERENCE TO RELATED APPLICATIONS

This application is a continuation of and claims priority to U.S. application Ser. No. 12/703,267 filed Feb. 10, 2010 now U.S. application patent Ser. No. 8,193,085, which is a divisional of U.S. application Ser. No. 11/090,104 filed Mar. 24, 2005 now U.S. application patent Ser. No. 7,701,071, the contents of which are herein incorporated by reference in its entirety.

FIELD

Embodiments of the invention are related in general to the field of electronic systems and semiconductor devices and more specifically to methods for fabricating flip-assembled and underlined semiconductor devices.

DESCRIPTION OF THE RELATED ART

When an integrated circuit (IC) chip is assembled on an insulating substrate with conducting lines, such as a printed circuit motherboard, by solder bump connections, the chip is spaced apart from the substrate by a gap; the solder bump interconnections extend across the gap. The IC chip is typically a semiconductor such as silicon, silicon germanium, or gallium arsenide, the substrate is usually made of ceramic or polymer-based materials such as FR-4. Consequently, there is a significant difference between the coefficients of thermal expansion (CTE) of the chip and the substrate; for instance, with silicon (about 2.5 ppm/° C.) as the semiconductor material and plastic FR-4 (about 25 ppm/° C.) as substrate material, the difference in CTE is about an order of magnitude. As a consequence of this CTE difference, thermomechanical stresses are created on the solder interconnections, especially in the regions of the joints, when the assembly is subjected to temperature cycling during device usage or reliability testing. These stresses tend to fatigue the joints and the bumps, resulting in cracks and eventual failure of the assembly.

In order to distribute the mechanical stress and to strengthen the solder joints without affecting the electrical connection, the gap between the semiconductor chip and the substrate is customarily filled with a polymeric material, which encapsulates the bumps and fills any space in the gap. For example, in the well-known "C-4" process developed by the International Business Machines Corporation, polymeric material is used to fill any space in the gap between the silicon chip and the ceramic substrate.

The encapsulant is typically applied after the solder bumps have undergone the reflow process and formed the metallic joints for electrical contact between the IC chip and the substrate. A viscous polymeric, thermoset precursor, sometimes referred to as the "underfill", is dispensed onto the substrate adjacent to the chip and is pulled into the gap by capillary forces. The precursor is then heated, polymerized and "cured" to form the encapsulant; after the curing process, the encapsulant is hard and cannot be softened again.

It is well known in the industry that the temperature cycling needed for the underfill curing process can create thermomechanical stress on its own, which may be detrimental to the chip and/or the solder interconnections. Additional stress is created when the assembly is cooled from the reflow temperature to ambient temperature. The stress created by these process steps may delaminate the solder joint, crack the passivation of the chip, or propagate fractures into the circuit structures. In general, the sensitivity to cracking of the layered structures of integrated circuits is increasing strongly with decreasing thickness of the various layers and increasing mechanical weakness of low dielectric constant insulators.

SUMMARY

Consequently, a need has arisen for an assembly methodology in which the stress-distributing benefits of the underfill material can be enjoyed without the deleterious side-effects of the underfilling process, resulting in enhanced device reliability. It is a technical advantage if the methodology provides an opportunity for device repair or re-working. The methodology should be coherent, low-cost, and flexible enough to be applied to different semiconductor product families and a wide spectrum of design and process variations. It is another technical advantage, if these innovations are accomplished while shortening production cycle time and increasing throughput.

One embodiment of the invention is a tape for use as a carrier, which comprises a base sheet of polymeric, preferably thermoplastic, material having first and second surfaces. A first polymeric adhesive film and a first foil of different material are attached to the base sheet on both the first and second surface sides; they thus provide a partial thickness to the tape. Further, a second polymeric adhesive film and a second foil of different material are attached to the first foil on the second surface side. A plurality of holes is formed through the partial thickness of the tape; and a reflow metal element is placed in each of the holes; the element adheres to the second adhesive film, and has preferably a diameter about equal to the partial thickness.

Another embodiment of the invention is a semiconductor device, which comprises a workpiece with an outline and plurality of contact pads and further an external part with a plurality of terminal pads. This part is spaced from the workpiece, and the terminal pads are aligned with the workpiece contact pads, respectively. A reflow element interconnects each of the contact pads with its respective terminal pad. Thermoplastic material fills the space between the workpiece and the part; this material adheres to the workpiece, the part and the reflow elements. Further, the material has an outline substantially in line with the outline of the workpiece, and fills the space substantially without voids.

When the workpiece is a semiconductor chip, the external part is a substrate suitable for flip-assembly of the chip. When the workpiece is a semiconductor package encapsulating an assembled semiconductor chip, the external part is board suitable for flip-attachment of the package.

Due to the thermoplastic character of the filling material, the finished device can be reworked, when the temperature range for reflowing the reflow elements is reached.

Another embodiment of the invention is a method for assembling a semiconductor device, in which a workpiece with an outline and a plurality of contact pads is provided, further a tape as described above; the location of the holes, and thus the reflow metal elements in the holes, match the locations the contact pads. The first foil is removed from the first tape surface side, whereby the first polymeric adhesive film on the first tape side is exposed. The reflow elements of the tape are then placed in contact with the contact pads of the workpiece such that the first polymeric adhesive film on the first tape side holds the workpiece in place. Thermal energy is supplied to the workpiece and the tape sufficient to reflow the reflow elements and liquefy the thermoplastic base sheet.

After cooling to ambient temperature, the tape is attached to the workpiece substantially without leaving voids.

The process steps of the method may continue by providing an external part with a plurality of terminal pads in locations matching the locations of the reflow elements in the tape holes. The second foil is removed, together with the second polymeric adhesive film and the first foil, from the second surface side, whereby the first polymeric adhesive film on the second tape side is exposed. The reflow elements of the tape are then placed in contact with the terminal pads of the external part such that the first polymeric adhesive film on the second tape side holds the external part in place. Thermal energy is supplied to the workpiece, the tape, and the external part sufficient to reflow the reflow elements and liquefy the thermoplastic base sheet. After cooling to ambient temperature, the tape is attached to the external part, while the workpiece is spaced apart from the external part and the space is filled substantially without leaving voids.

When the workpiece is a semiconductor chip, the external part is a substrate suitable for flip-assembly of the chip. When the workpiece is a semiconductor wafer containing a plurality of semiconductor devices, the external part is a substrate suitable for flip-assembly of the wafer. When the workpiece is a semiconductor package, which encapsulates an assembled semiconductor chip, the external part is a board suitable for flip-attachment of the package. When the workpiece is a stack of semiconductor packages, the external part is a board suitable for flip-attachment of the stack.

Embodiments of the present invention are related to flip-chip assemblies, ball grid array packages, chip-scale and chip-size packages, and other devices intended for reflow attachment to substrates and other external parts. It is a technical advantage that the invention offers a methodology to reduce the thermomechanical stress between the semiconductor part of a device and a substrate of dissimilar thermal expansion coefficient while concurrently controlling essential assembly parameters such as spacing between the semiconductor part and the substrate, adhesion between the parts, and selection of the temperature ranges needed in the assembly process. Additional technical advantages derive from the fact that the devices made with the thermoplastic tape are reworkable. Further, the process flow is simplified since the conventional underfill process after the flip-assembly is eliminated.

The technical advantages represented by certain embodiments of the invention will become apparent from the following description of the preferred embodiments of the invention, when considered in conjunction with the accompanying drawings and the novel features set forth in the appended claims.

DETAILED DESCRIPTION OF THE PREFERRED EMBODIMENTS

Figure 1:
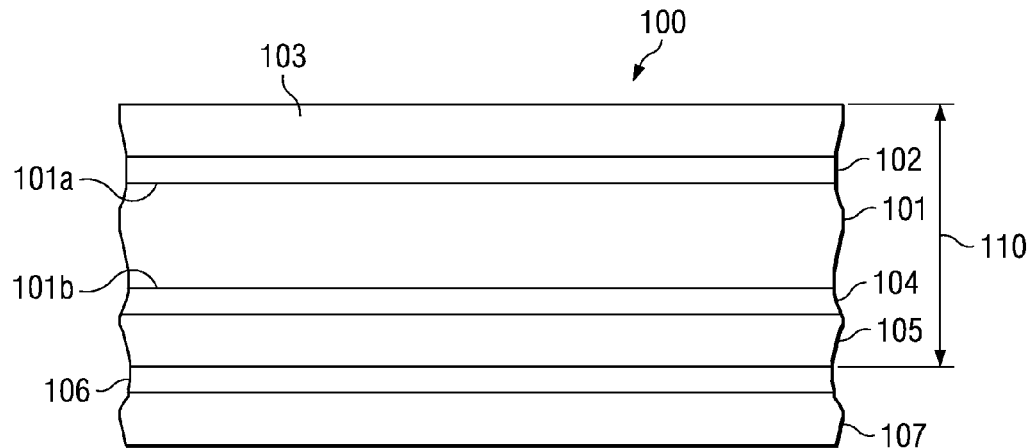
FIG. 1 shows schematically the cross section of a tape for use in semiconductor assembly in order to illustrate the structure of various insulating and adhesive layers according to the invention.

One embodiment of the invention is depicted in the schematic cross section of FIG. 1 as a tape, generally designated 100, for use as a carrier and specifically in semiconductor device assembly. Tape 100 comprises a base sheet 101 of polymeric, preferably thermoplastic material in the thickness range from about 25 to 450 µm; for some devices, the thickness may reach approximately 800 µm. Preferred thermoplastic base sheet materials include long-chain polyimides with acrylic resin or silicone resin, long-chain polyethylenes with acrylic resin, and long-chain polypropylenes with acrylic resin. The base sheet material is preferably selected so that it softens and enters the low viscosity or liquid phase in the same temperature range, which is needed for reflowing the reflow element embedded in the tape (see below). This temperature range includes, for example, the melting temperature of the solder selected for assembling the device. It is a technical advantage, when the base sheet is selected from thermoplastic materials, since the processes of liquefying and solidifying the thermoplastic material may be repeated numerous times without difficulty. Preferably, the coefficient of thermal expansion is selected between about 8 and 120 ppm, and the elasticity modulus between about 100 and 10000 MPa.

Base sheet 101 has a first surface 101a and a second surface 101b. Attached to the first surface 101a are a first polymeric adhesive film 102 followed by a first foil 103 of different material. In similar fashion, attached to the second surface 101b are a first polymeric adhesive film 104 followed by a first foil 105 of different material. The adhesive films 102 and 104 preferably include polymer materials such as epoxy, polyimide, or silicone, which have not only adhesive properties, but can also easily be peeled off; the adhesive films have a preferred thickness range from about 25 to 100 μm. The foils 103 and 105 comprise inert materials such as PVC and PET, and have a preferred thickness range from about 25 to 50 μm.

The combination of the base sheet 101, the polymeric adhesive films 102 and 104, and the foils 103 and 105 provides a partial thickness 110 to tape 100. It is this partial thickness 110, which is penetrated by a plurality of holes in tape 100 in order to provide space for reflow elements such as solder balls (see FIGS. 2 and 4).

As FIG. 1 shows, tape 100 further comprises a second polymeric adhesive film 106 attached to the first foil 105 on the second surface side of the base sheet, followed by a second foil 107. The second polymeric adhesive film 106 is preferably selected from materials such as epoxy, polyimide, and silicone in the thickness range from about 25 to 100 μm. The second foil 107 is preferably an inert material such as PVC and PET in the thickness range from about 10 to 50 μm. Laminated tapes such as tape 100 are commercially available and can be made to custom specification, for instance by the company Lintec, Japan.

Figure 2:
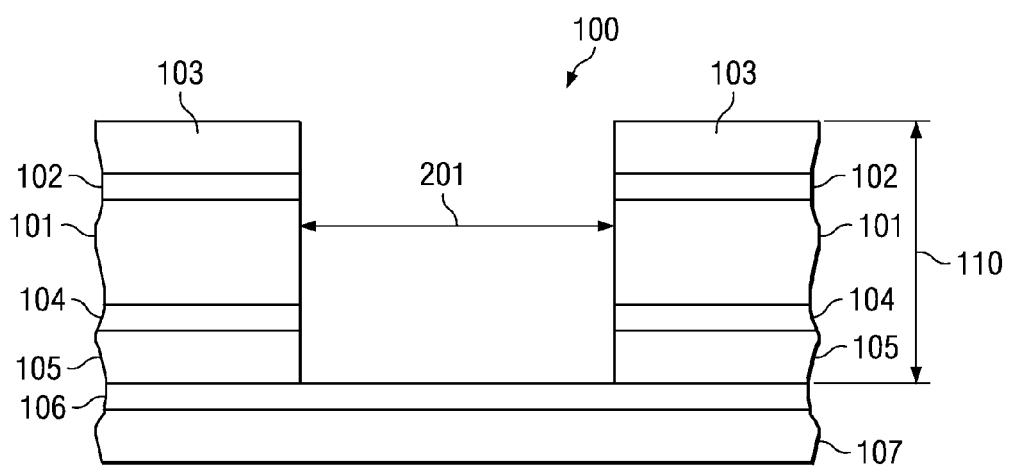
FIG. 2 shows schematically the cross section of the tape of FIG. 1 having a hole with substantially vertical walls, formed to partially penetrate the thickness of the tape.
Figure 3:
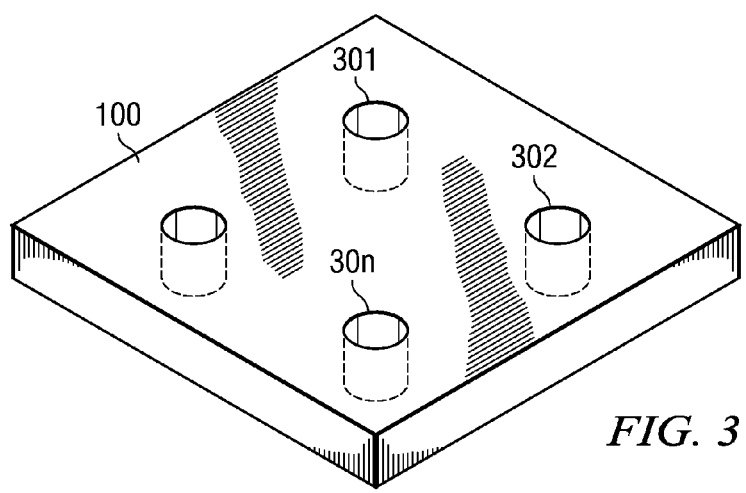
FIG. 3 is a schematic and simplified perspective view of the tape, showing a plurality of holes.

As FIG. 3 schematically illustrates, a plurality of holes 301, 302, . . . , 30n is formed in tape 100. The position of these holes can be selected in any predetermined pattern. FIG. 2 shows one specific hole of diameter 201 in more detail. The hole penetrates the laminated tape 100 to the depth 110, which is defined in FIG. 1. Depth 110 reaches to the second polymeric adhesive film 106, but does not penetrate it fully. Among the techniques available for the opening processes are laser, mechanical drill, and mechanical punching. Experience has shown that the laser technique is superior to the drilling or punching techniques. The preferred laser method is excimer laser, because excimer laser has an accuracy of +/−5 μm for defining the depth 110 and the diameter 201. The hole may be round or may have any other predetermined outline; the hole diameter may be same for all holes, or it may be different.

Figure 4:
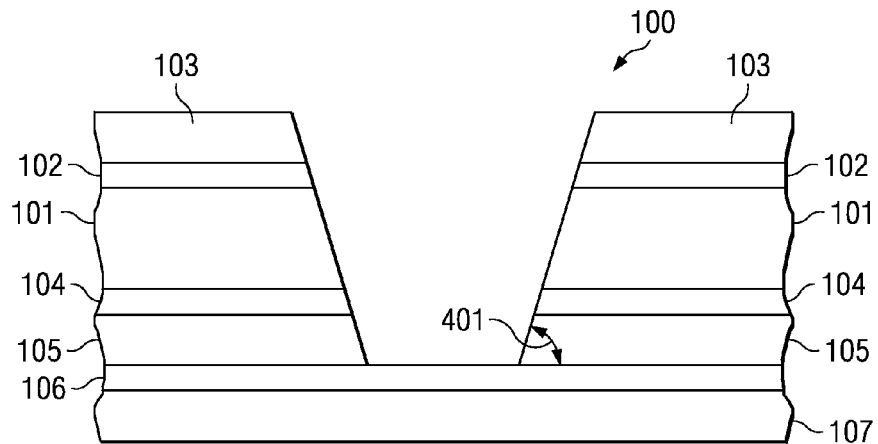
FIG. 4 shows schematically the cross section of the tape of FIG. 1 having a hole with tapered walls, formed to partially penetrate the thickness of the tape.

The hole illustrated in FIG. 2 is shown to have approximately vertical walls. However, for certain applications such as stable fitting of solder balls, tapered walls as illustrated in FIG. 4 may be preferable. The tapered walls form an angle 401 with second adhesive film 106. The preferred angle 401 is between about 70° and 80°.

Figure 5:
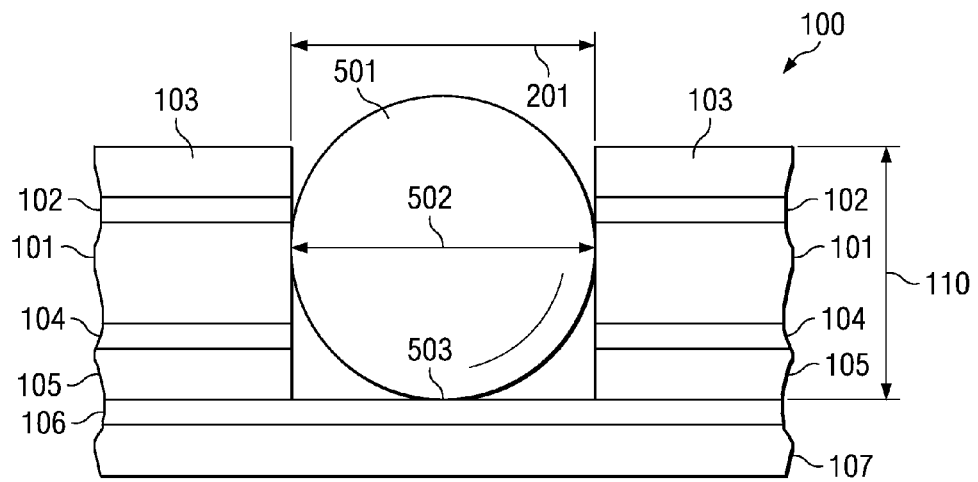
FIG. 5 is a cross section of the tape of FIG. 2 with an element of reflow metal positioned in the hole of the tape.
Figure 6:
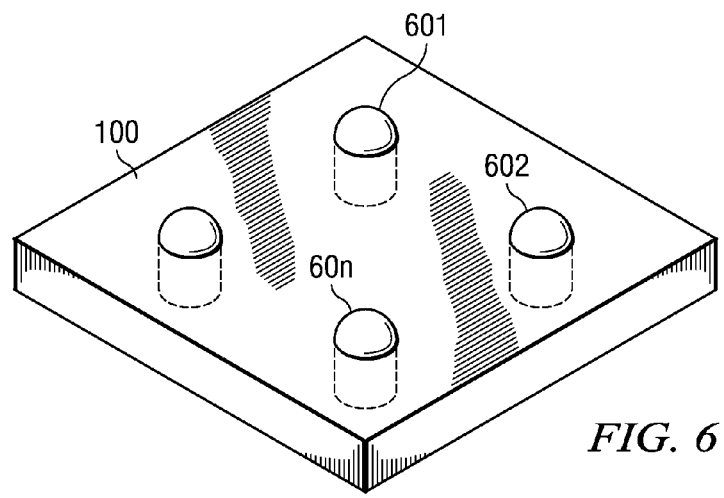
FIG. 6 is a schematic and simplified perspective view of the tape of FIG. 3 with an element of reflow metal positioned in each hole.

FIG. 6 illustrates how one reflow metal element is placed in each of the holes in tape 100. As an example, the reflow elements may be solder balls 601, 602, . . . , 60n. FIG. 5 shows one specific reflow metal element 501 in more detail in a hole of depth 110. Reflow element 501 has preferably a diameter 502 equal to or slightly less than the hole diameter 201. In area 503, reflow element 502 is in contact with second polymeric adhesive film 106 of tape 100; in this fashion, reflow element 501 is securely held in place in the hole and cannot be dislodged or fall out, even when the tape is positioned upside down relative to the position illustrated in FIG. 5 so that the hole opening with the reflow element faces downward.

In order to highlight the technically superior features of tape 100, FIGS. 7 through 20 describe various process steps of assembly and device fabrication employing a workpiece, which has an outline and a plurality of contact pads. The tape is provided with the plurality of holes and inserted reflow elements in locations, which match the locations of the contact pads of the workpiece. In embodiments for the semiconductor industry, the workpiece is either a semiconductor wafer containing a plurality of semiconductor devices, or a semiconductor chip, or a semiconductor package, which encapsulates an assembled semiconductor chip on a substrate.

Figure 7:
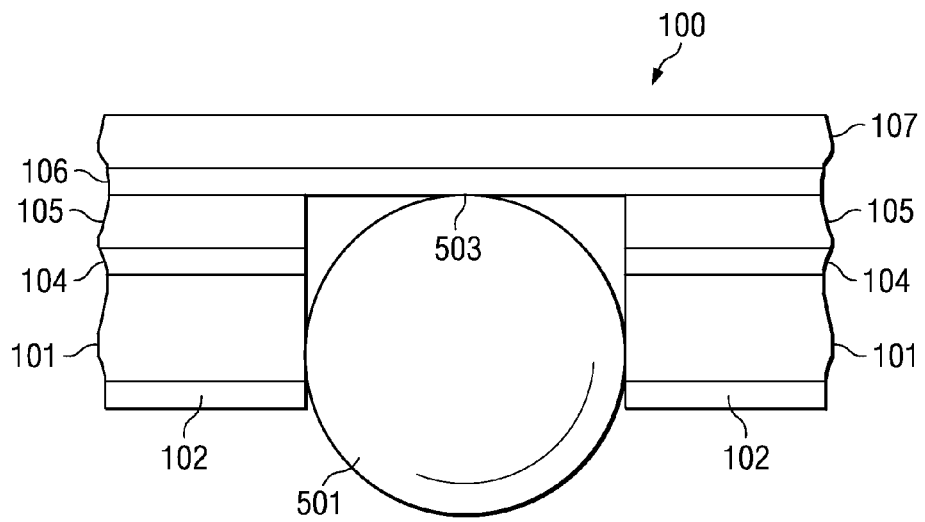
FIG. 7 shows a schematic cross section of the tape of FIG. 5 after removal of the outermost layer of the tape structure.

The process flow starts with FIG. 7, wherein the first foil 103 has been removed and the position of the hole with the inserted reflow element is inverted relative to the starting position in FIG. 5. First polymeric adhesive film 102 is now exposed. Reflow element 501 remains firmly in place, since it is in contact with polymeric adhesive film 106 in area 503. For many applications, the size of element 501 and the hole have been selected so that element 501 is slightly protruding from the hole at this stage of the process flow.

Figure 8:
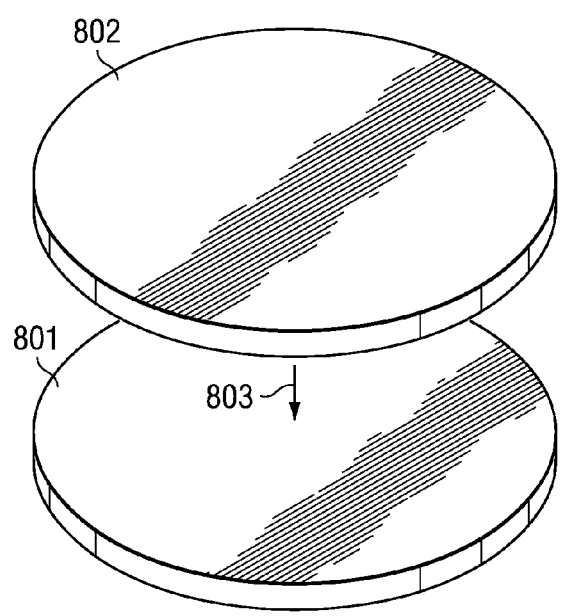
FIG. 8 is a schematic perspective view of a tape structured as shown in FIG. 7 in the process of being attached to a circular workpiece, such as a semiconductor wafer.

As a specific workpiece, the schematic FIG. 8 shows in perspective view a semiconductor wafer 801 with the plurality of semiconductor devices facing upward. Each device has a plurality of contact pads, facing upward. Tape 802 is positioned upside down as shown in the portion of FIG. 7; the locations of the plurality of reflow elements in the tape holes match the locations of the contact pads of the semiconductor devices on the wafer. As arrow 803 indicates, each reflow element of tape 802 is brought into contact with its corresponding contact pad of wafer 801. For this embodiment, tape 802 has preferably the same outline as the semiconductor wafer 801.

Figure 10:
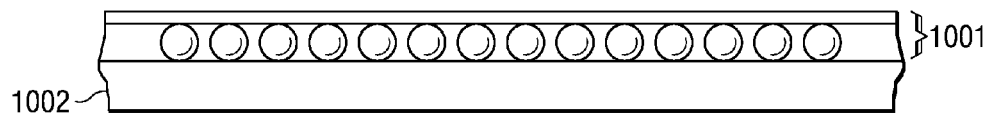
FIG. 10 is a schematic cross section of a portion of the tape attached to a workpiece such as a semiconductor wafer.

The simplified cross section of FIG. 10 illustrates tape 1001 contacting workpiece 1002; as stated above, workpiece 1002 may be specifically a semiconductor wafer. At this stage, the assembly is ready for the next process step of heating (see below).

Figure 9:
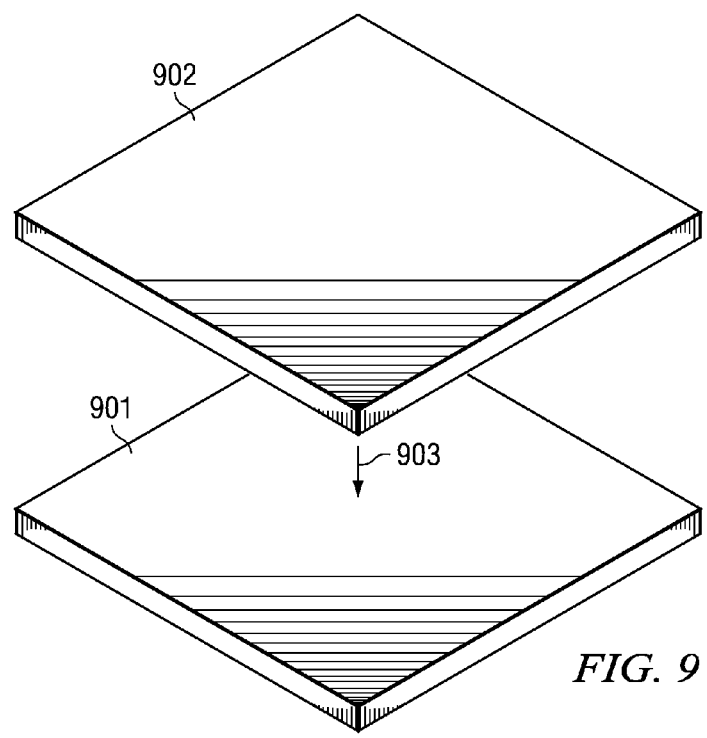
FIG. 9 is a schematic perspective view of a tape structured as shown in FIG. 7 in the process of being attached to a rectangular workpiece, such as a board-like entity containing a plurality of assembled and encapsulated semiconductor chips.

As another specific workpiece, the schematic FIG. 9 shows a molded entity 901 containing a plurality of semiconductor chips assembled on a substrate and encapsulated by molding compound. The substrate has a plurality of contact pads for each assembled chip, facing upward. Tape 902 is positioned upside down as shown in the portion of FIG. 7; the locations of the plurality of reflow elements in the tape holes match the locations of the contact pads of the substrate of the molded entity 901. As arrow 903 indicates, each reflow element of tape 902 is brought into contact with its corresponding contact pad of molded entity 901. For this embodiment, tape 902 has preferably the same outline as the molded entity 901.

Figure 11:
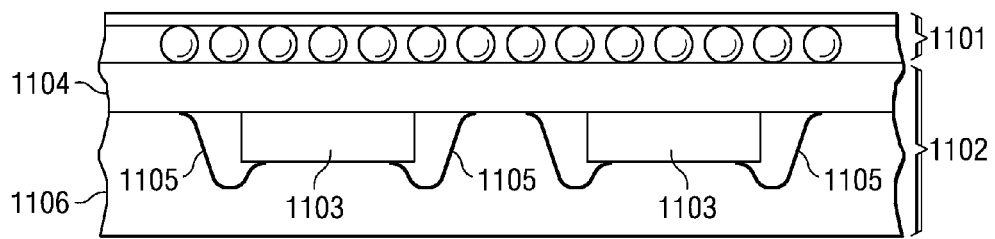
FIG. 11 is a schematic cross section of a portion of the tape attached to a workpiece such as a board-like entity containing a plurality of assembled and encapsulated semiconductor chips.

The simplified cross section of FIG. 11 illustrates tape 1101 contacting workpiece 1102; as stated above, workpiece 1102 may be specifically a molded semiconductor entity containing a plurality of assembled semiconductor chips 1103 on a substrate 1104; the chips 1103 are connected to substrate 1104 by bonding wires 1105 and encapsulated by molding compound 1106. At this stage, the assembly is ready for the next process step of heating (see below).

Figure 12:
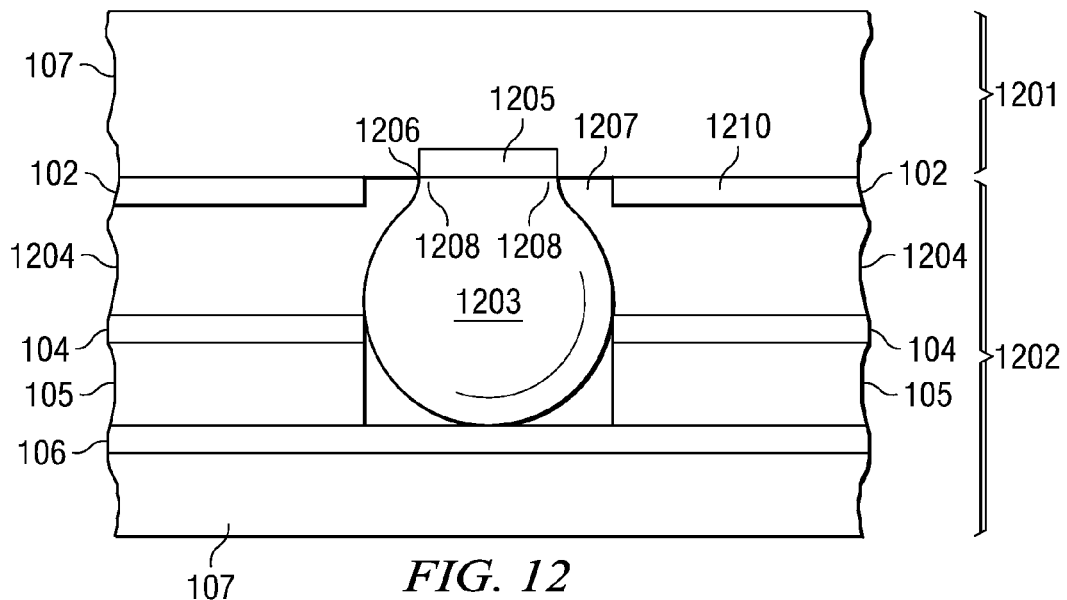
FIG. 12 is a schematic cross section illustrating a portion of the tape assembled on a workpiece as shown in FIG. 10 in a position inverted relative to the position in FIG. 10.
Figure 13:
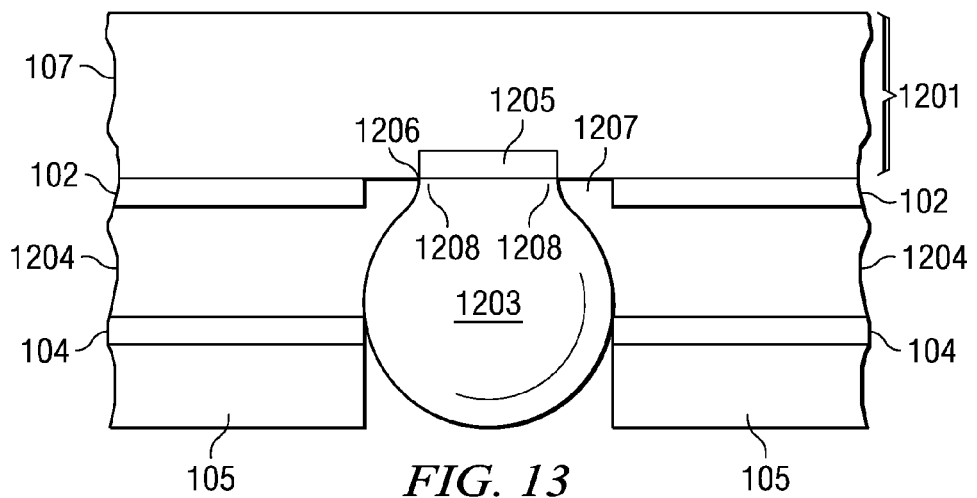
FIG. 13 is a schematic cross section illustrating the tape portion of FIG. 12 after removal of certain layers of the tape in order to expose the attached reflow element.

The schematic cross section of FIG. 12 illustrates the next step of the fabrication process. Each reflow element 1203 of the tape is brought into contact with the respective contact pad 1205 of the workpiece; for example, the workpiece may be a semiconductor chip or a semiconductor package. This step may be facilitated by the first polymeric adhesive film 102 holding workpiece 1201 in place. Thermal energy is then supplied to workpiece 1201 and tape 1202 sufficient to reflow the reflow element 1203 and liquefy the thermoplastic base sheet 1204 (designated 101 in FIG. 1 before liquefying), whereby tape 1202 is attached to workpiece 1201. In FIG. 12, the effect of the heating cycle is schematically indicated by two results: The reflow element (for example, solder ball) has formed a joint 1206 across the whole length of pad 1205, while the remaining surface of the element has been pulled by surface tension into an approximately spherical shape. The softened thermoplastic material 1204 has filled the available space 1207 around joint 1206 and the reflowed metal neck 1208. By selecting the appropriate heating temperature and time, the surrounding thermoplastic material is filling space 1207 substantially without leaving voids.

When those embodiments, in which the workpiece is an individual chip or an individual package, have been cooled to ambient temperature, the thermoplastic material has formed an outline, which is substantially in line with the outline of the workpiece. As defined herein, "in line" does not only include straight line, continuing the outline of the workpiece; it also includes minor concave or convex contours. However, "in line" excludes the well-known meniscus, which is typically formed in conventional technology by dispensing thermoset underfill material. In the conventional fabrication process, the low-viscosity thermoset material is driven by surface tension to protrude somewhat outside the workpiece contours to form the well-known meniscus.

In the next process step, the second foil 107 and the second polymeric adhesive film 106 are removed, exposing the approximately spherical shape of the reflow element 1203. The result is displayed in FIG. 13. In the next process step, the first foil 105 from the second tape surface side is removed, exposing the first polymeric adhesive film 104 on the second side of tape 1204. The result is displayed in FIG. 14.

Figure 14:
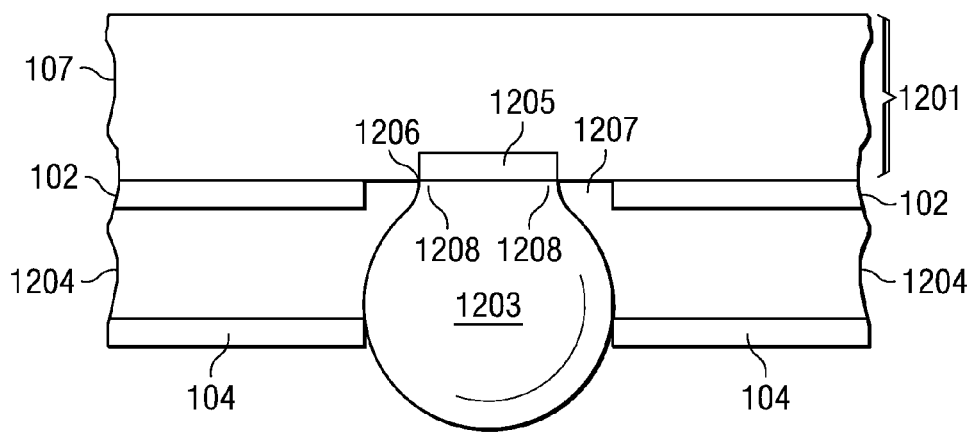
FIG. 14 is a schematic cross section illustrating the tape portion of FIG. 13 after removal of additional layers of the tape.
Figure 15:
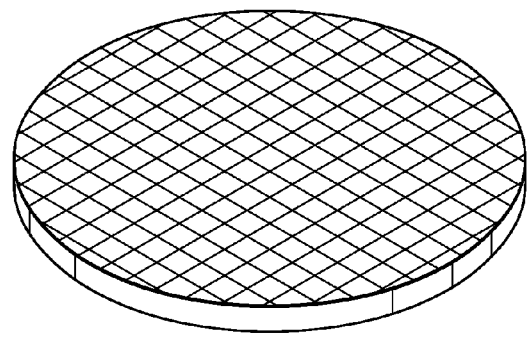
FIG. 15 is a schematic top view of the tape attached to a circular workpiece after the process step of dicing.

When workpiece 1201 is not an individual semiconductor chip, but a whole semiconductor wafer containing a plurality of semiconductor devices, the next process step after the stage shown in FIG. 14 comprises the separation of the wafer, assembled with the tape, into discrete assembled devices. The preferred method of separation is sawing. The schematic top view of FIG. 15 illustrates the result of this step.

Figure 16:
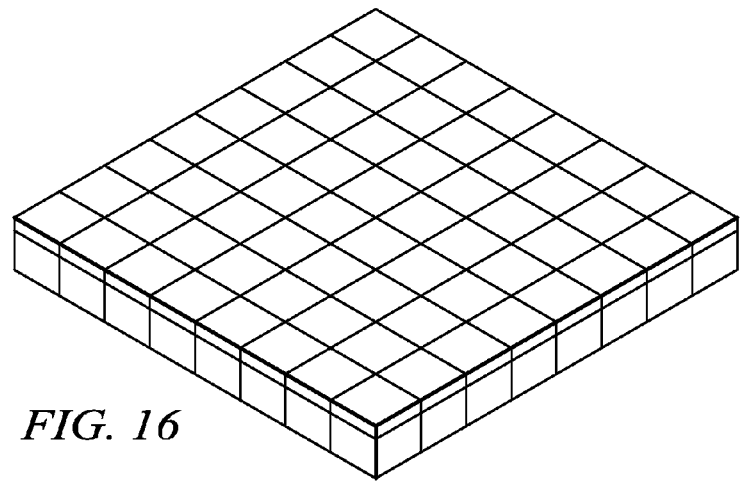
FIG. 16 is a schematic perspective view of the tape attached to a rectangular workpiece after the process step of dicing.

When workpiece 1201 is not an individual semiconductor package, but a whole molded entity containing a plurality of assembled and encapsulated semiconductor chips, the next process step after the stage shown in FIG. 14 comprises the separation of the entity, assembled with the tape, into discrete assembled devices. The preferred method of separation is sawing. The schematic perspective view of FIG. 16 illustrates the result of this step.

For the next process step, an external part is provided, which has a plurality of terminal pads in locations matching the locations of the reflow elements. As an example, the external part may be a substrate suitable for flip-assembly of the semiconductor chip, which has previously been attached to the tape. As another example, the external part may be a substrate suitable for flip-assembly of a whole semiconductor wafer. As yet another example, the external part may be a board suitable for flip-assembly of the semiconductor package, which has previously been attached to the tape.

Figure 17:
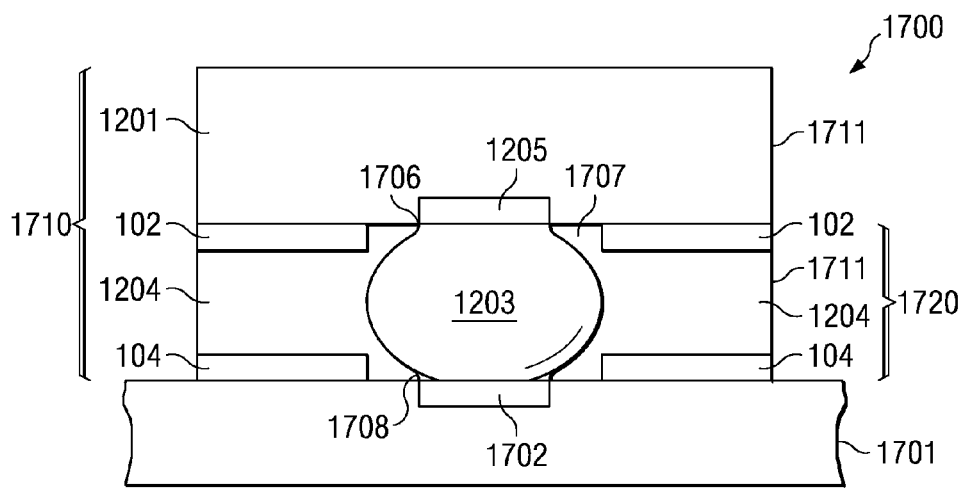
FIG. 17 is a schematic cross section illustrating a singulated tape unit with a reflow element, assembled on an external part.

In FIG. 17, the external part is designated 1701, and one of the plurality of terminal pads is designated 1702. The workpiece 1201 with its contact pad 1205 together with the attached remainder 1720 of the tape and the reflow element form unit 1710. Notice that the side contours of unit 1710 are shown as substantially straight contours 1711; the straight contours 1711 are a consequence either of the singulation steps described above, or of the assembly using the tape with the thermoplastic base sheet.

The reflow element 1203 of the tape, soldered to workpiece contact pad 1205, is placed in contact with the terminal pad 1702 of the external part. In addition, the first polymeric adhesive film 104 on the second tape side may hold the external part 1701 in place. Thermal energy is then supplied to the workpiece 1201, the tape 1720, and the external part 1701 sufficient to reflow the reflow element 1203 and to liquefy the thermoplastic base sheet 1204 of the tape 1720. In FIG. 17, the effect of the heating cycle is schematically indicated by two results: The reflow element 1203 has formed a joint 1706 across the whole length of terminal pad 1202; and the softened thermoplastic material 1204 has filled the available space 1707 around joint 1706 and the reflowed metal neck 1708. By selecting the appropriate heating temperature and time, the surrounding thermoplastic material is filling space 1707 substantially without leaving voids. Further, after cooling to ambient temperature, the thermoplastic material 1204 has approximately retained its outline 1711, which is substantially in line with the outline 1711 of the workpiece.

As a result of the assembly process, the tape 1720 and the workpiece 1201 are attached to the external part 1701, while the workpiece 1201 is spaced apart form the external part 1701. The thermoplastic "underfill" material is in place to mitigate thermo-mechanical stress at the reflow interconnection and the solder joints due to its insignificant thermal shrinkage compared to conventional thermoset underfill materials. The finished product is generally designated 1700 in FIG. 17.

For the assembly process steps described above, the materials for the polymeric adhesive films 102, 104, and 106 are preferably selected so that they remain sticky in the temperature range from ambient temperature to about 300° C. and even higher, do not require a specific curing process, and have a decomposition temperature above about 300° C.

It is evident from the above description of the material selection and process flow that no flux is required for the metal reflow and soldering action, and any process-related stress on the metal reflow ball during the temperature cycles is minimized due to the continued presence of the thermoplastic polymer. Further, the thermoplastic material fills any available space substantially void-free. Experience has further shown that the choice of thermoplastic material and its continued presence during the fabrication process provides the semiconductor products with characteristics of reliability performances under use conditions as well as tests of temperature cycling, moisture sensitivity, and drop examinations, which are three to ten times higher than products manufactured using prior art fabrication technologies.

Figure 18:
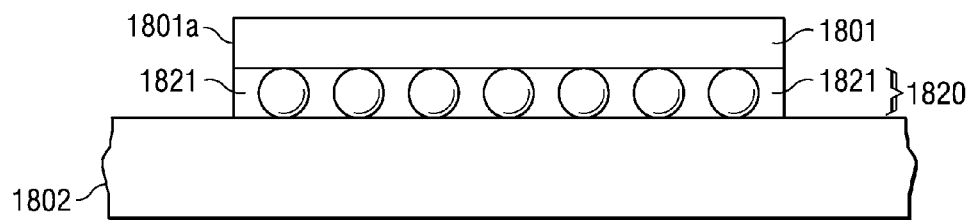
FIG. 18 exemplifies in a schematic cross section the assembled unit of FIG. 17 as a semiconductor chip flip-attached onto an external board.

The schematic FIG. 18 is an example of an embodiment, in which the workpiece is a semiconductor chip 1801 flip-attached by means of tape 1820 onto an external board 1802. In the reflow process step, the solder joint formation and the substantially void-free underfilling are performed concurrently. Notice that the tape 1820 has an outline 1821 substantially in line with the outline 1801a of the chip 1801. This approximately straight outline is a consequence of the thermoplastic nature of the tape base material; for a chip singulated from a wafer it may also be created by the chip separation process.

Figure 19:
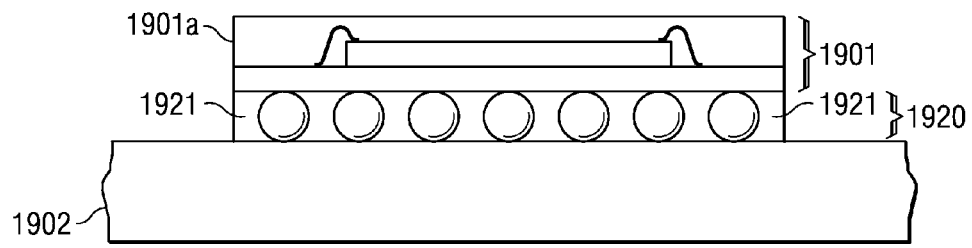
FIG. 19 exemplifies in a schematic cross section the assembled unit of FIG. 17 as a semiconductor package comprising an encapsulated device flip-attached onto an external board.

The schematic FIG. 19 is an example of an embodiment, in which the workpiece is a semiconductor package 1901 having a substrate 1902 with terminal pads, which are attached by means of tape 1920 onto an external board 1902. In the reflow process step, the solder joint formation and the substantially void-free underfilling are performed concurrently. Notice that the tape 1920 has an outline 1921 substantially in line with the outline 1901a of the package 1901. This approximately straight outline is a consequence of the thermoplastic nature of the tape base material; for a package singulated from a molded entity it may also be created by the package separation process.

Figure 20:
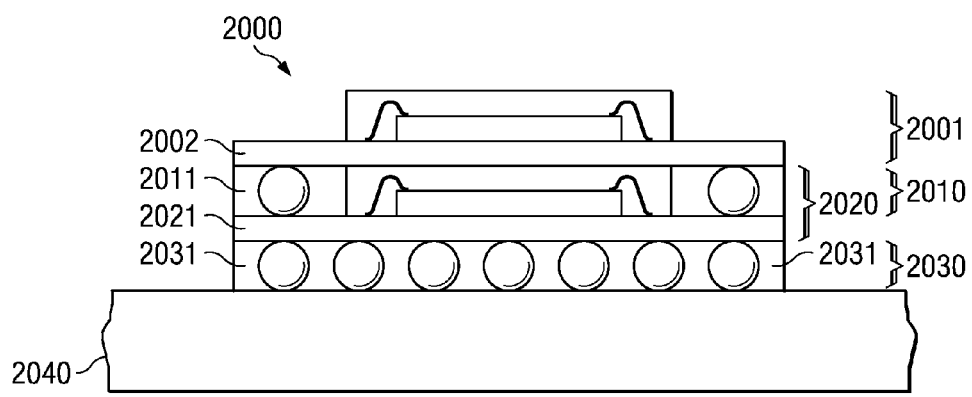
FIG. 20 is a schematic cross section of a stack of semiconductor packages flip-attached onto an external board using the assembly tape of the invention.

Another embodiment, a semiconductor product generally designated 2000, is displayed in the schematic FIG. 20. A first package 2001 having an extended substrate 2002 is attached by means of tape 2010 to a second package 2020, also having an extended substrate 2021. The stack of two packages is attached by means of tape 2030 to an external part such as a board 2040. The use of thermoplastic material in the base sheet of tapes 2010 and 2030 enables a substantially straight outline 2011 and 2031. Stacks of packages are generally known to be sensitive to thermo-mechanical stress due to the distributed components of widely different coefficients of thermal expansion (silicon, metals, polymers, etc.). It is, therefore, a particular technical advantage of the invention to offer a stack structure and fabrication method based on thermoplastic underfill material, which reduces thermo-mechanical stress significantly by having a much smaller thermal shrinking than the thermoset materials of conventional art. With this advantage, it is easy for someone skilled in the art to construct composite devices in view of FIG. 20, which can be realized by the concept and method of the invention.

While this invention has been described in reference to illustrative embodiments, this description is not intended to be construed in a limiting sense. Various modifications and combinations of the illustrative embodiments, as well as other embodiments of the invention, will be apparent to persons skilled in the art upon reference to the description. As an example, for assemblies having interconnection elements with significantly higher or lower reflow temperatures, suitable base sheet thermoplastics and adhesives can be formulated by modifying the polymer chains of their materials. As another example, underfill materials of lower coefficients of thermal expansion can be formulated by adding inert (inorganic) fillers to the polymer base material. It is therefore intended that the appended claims encompass any such modifications and embodiments.

We claim:

1. A method for assembling a semiconductor device comprising:

providing a workpiece having an outline and a plurality of contact pads, each pad having a location;

providing a tape having a base sheet of thermoplastic material and first and second surfaces; a first polymeric adhesive film and a first foil of material different from the first polymeric adhesive film attached to said base sheet on said first and second surface sides, providing a partial thickness to said tape; a second polymeric adhesive film and a second foil of material different from the second polymeric adhesive film attached to said first foil on said second surface side; a plurality of holes, each having a location, through said partial thickness of said tape; a reflow metal element in each of said holes, adhering to said second polymeric adhesive film, and thus said reflow metal elements in said holes, the locations of said holes matching the locations of said contact pads;

removing said first foil from said first tape surface side, exposing said first polymeric adhesive film on said first tape side;

placing said reflow elements of said tape in contact with said contact pads of said workpiece;

supplying thermal energy to said workpiece and said tape sufficient to reflow said reflow elements and liquefy said thermoplastic base sheet;

cooling said workpiece and said tape to ambient temperature, thus attaching said tape to said workpiece;

providing an external part having a plurality of terminal pads in locations matching the locations of said reflow elements in said tape holes;

removing said second foil, said second polymeric adhesive film, and said first foil from said second surface side, exposing said first polymeric adhesive film on said second tape side;

placing said reflow elements of said tape in contact with said terminal pads of said external part such that said first polymeric adhesive film on said second tape side holds said external part in place;

supplying thermal energy to said workpiece, said tape, and said external part sufficient to reflow said reflow elements and liquefy said thermoplastic base sheet; and cooling said workpiece, said tape, and said external part to ambient temperature, thus attaching said tape to said external part, while spacing said workpiece apart from said external part.

2. The method according to claim 1 wherein said process step of contacting reflow elements and respective contact pads is facilitated by said first adhesive film on said first tape side holding said workpiece in place.

3. The method according to claim 1 wherein said liquefied thermoplastic base sheet surrounds said reflow elements substantially without voids.

4. The method according to claim 1 wherein said liquefied thermoplastic base sheet fills said space between said workpiece and said external part substantially without voids.

5. The method according to claims 1 wherein said workpiece is a semiconductor chip, and said external part is a substrate suitable for flip-assembly of said chip.

6. The method according to claims 1 wherein said workpiece is a semiconductor wafer containing a plurality of semiconductor devices, and said external part is a substrate suitable for flip-assembly of said wafer.

7. The method according to claim 6 further comprising the step of separating said assembled wafer into discrete assembled chips, thereby singulating semiconductor devices.

\* \* \* \* \*